United States Patent
Jeffrey et al.

(10) Patent No.: US 9,352,120 B2
(45) Date of Patent: May 31, 2016

(54) CATHETER WITH ENHANCED PUSHABILITY

(75) Inventors: Andrew Jeffrey, Tuebingen (DE); John P. Lacken, Pforzheim (DE)

(73) Assignee: ABBOTT LABORATORIES VASCULAR ENTERPRISES LIMITED, Dublin (IE)

( * ) Notice: Subject to any disclaimer, the term of this patent is extended or adjusted under 35 U.S.C. 154(b) by 0 days.

(21) Appl. No.: 13/386,880

(22) PCT Filed: Jul. 29, 2010

(86) PCT No.: PCT/EP2010/004654
§ 371 (c)(1),
(2), (4) Date: Aug. 6, 2012

(87) PCT Pub. No.: WO2011/012308
PCT Pub. Date: Feb. 3, 2011

(65) Prior Publication Data
US 2012/0316585 A1    Dec. 13, 2012

(30) Foreign Application Priority Data

Jul. 29, 2009  (EP) ..................................... 09009804

(51) Int. Cl.
*A61M 25/10* (2013.01)
*A61M 25/00* (2006.01)

(52) U.S. Cl.
CPC ......... *A61M 25/005* (2013.01); *A61M 25/0051* (2013.01); *A61M 25/1006* (2013.01); *A61M 2025/0059* (2013.01)

(58) Field of Classification Search
CPC .................. A61M 1/1072; A61M 2025/1004; A61M 2025/1068; A61M 2025/1093; A61M 25/0054; A61M 25/0138; A61M 25/1002; A61M 25/1011; A61M 25/1027; A61M 25/1038

USPC ......... 604/96.01, 103.09–103.11, 1.49, 1.11, 604/194, 99.04; 623/1.11, 1.49
See application file for complete search history.

(56) References Cited

U.S. PATENT DOCUMENTS 4,276,874 A * 7/1981 Wolvek et al. .................. 600/18
4,813,934 A * 3/1989 Engelson et al. .......... 604/99.02
(Continued)

FOREIGN PATENT DOCUMENTS

EP          0452901          10/1991
EP     0 551 184 A1 *   7/1993
(Continued)

OTHER PUBLICATIONS

Patency. (2000). In Collins English Dictionary. Retrieved from http://www.credoreference.com/entry/hcengdict/patency. Nov. 7, 2013.*
(Continued)

*Primary Examiner* — Kami A Bosworth
*Assistant Examiner* — Matthew A Engel
(74) *Attorney, Agent, or Firm* — Workman Nydegger; John Kwok

(57) ABSTRACT

Apparatus for enhancing pushability and minimizing kinking of a balloon catheter is provided, wherein a catheter comprises inner and outer tubes, and a balloon that is proximally affixed to the outer tube and distally affixed to the inner tube. The catheter of the present invention further comprises a tubular member imposed on the inner tube which is configured to form a reversible mechanical linkage between inner tube and outer tube while an axially compressive load is applied to the catheter tip.

2 Claims, 4 Drawing Sheets

(56) References Cited

U.S. PATENT DOCUMENTS

| | | | | |
|---|---|---|---|---|
| 5,035,694 A * | 7/1991 | Kasprzyk | A61B 18/08 |
| | | | 604/913 |
| 5,035,705 A * | 7/1991 | Burns | 606/194 |
| 5,047,045 A | 9/1991 | Arney et al. | |
| 5,085,636 A | 2/1992 | Burns | |
| 5,156,594 A | 10/1992 | Keith | |
| 5,176,637 A * | 1/1993 | Sagae | A61M 25/104 |
| | | | 604/103.09 |
| 5,195,971 A | 3/1993 | Sirhan | |
| 5,221,260 A * | 6/1993 | Burns | A61M 25/0075 |
| | | | 604/913 |
| 5,370,615 A | 12/1994 | Johnson | |
| 5,492,532 A * | 2/1996 | Ryan et al. | 604/103.09 |
| 5,531,689 A * | 7/1996 | Burns et al. | 604/99.04 |
| 5,626,600 A | 5/1997 | Horzewski et al. | |
| 6,344,029 B1 * | 2/2002 | Estrada et al. | 604/103.09 |
| 6,540,721 B1 | 4/2003 | Voyles | |
| 6,706,010 B1 * | 3/2004 | Miki et al. | 604/43 |
| 6,712,767 B2 * | 3/2004 | Hossack et al. | 600/467 |
| 6,863,856 B1 * | 3/2005 | Mahoney | A61M 25/1029 |
| | | | 264/231 |
| 6,960,188 B2 * | 11/2005 | Jorgensen | 604/103.09 |
| 7,247,147 B2 * | 7/2007 | Nishide | A61M 25/104 |
| | | | 604/103.04 |
| 7,273,487 B1 * | 9/2007 | Duchamp | A61M 25/0045 |
| | | | 604/525 |
| 7,749,585 B2 * | 7/2010 | Zamore | 428/35.1 |
| 7,794,448 B2 * | 9/2010 | Grandt et al. | 604/524 |
| 7,815,627 B2 * | 10/2010 | Von Oepen et al. | 604/525 |
| 8,114,048 B2 * | 2/2012 | Pagel et al. | 604/96.01 |
| 8,460,168 B2 * | 6/2013 | Farnan | A61M 1/101 |
| | | | 600/16 |
| 2002/0095203 A1 * | 7/2002 | Thompson et al. | 623/1.11 |
| 2003/0055448 A1 * | 3/2003 | Lee | A61M 25/0069 |
| | | | 606/192 |
| 2003/0105426 A1 * | 6/2003 | Jorgensen | A61M 25/1006 |
| | | | 604/103.1 |
| 2004/0267280 A1 * | 12/2004 | Nishide | A61F 2/958 |
| | | | 606/108 |
| 2007/0016132 A1 * | 1/2007 | Oepen et al. | 604/96.01 |
| 2007/0118076 A1 * | 5/2007 | Lim | A61M 25/1029 |
| | | | 604/103.06 |
| 2007/0244550 A1 * | 10/2007 | Eidenschink | 623/1.49 |
| 2010/0249490 A1 * | 9/2010 | Farnan | A61M 1/101 |
| | | | 600/16 |
| 2012/0215167 A1 | 8/2012 | Pagel et al. | |

FOREIGN PATENT DOCUMENTS

| | | |
|---|---|---|
| EP | 0551184 | 7/1993 |
| EP | 1023913 | 8/2000 |
| GB | 2372211 | 8/2002 |
| WO | WO 03/035159 | 5/2003 |
| WO | WO 2005/096797 | 10/2005 |
| WO | WO2007054364 | 5/2007 |

OTHER PUBLICATIONS

U.S. Appl. No. 13/372,183, Feb. 26, 2013, Office Action.
U.S. Appl. No. 60/736,434, filed Nov. 14, 2005, Pagel et al.
U.S. Appl. No. 12/093,589, Mar. 19, 2010, Restriction Requirement.
U.S. Appl. No. 12/093,589, Jun. 9, 2010, Office Action.
U.S. Appl. No. 12/093,589, Nov. 10, 2010, Office Action.
U.S. Appl. No. 12/093,589, Oct. 7, 2011, Notice of Allowance.
U.S. Appl. No. 60/736,515, filed Nov. 14, 2005, Jeffrey et al.

* cited by examiner

CATHETER WITH ENHANCED PUSHABILITY

CROSS REFERENCE TO RELATED APPLICATIONS

This application is a U.S. Nationalization of PCT Application Number PCT/EP2010/004654, filed on Jul. 29, 2010, which claims priority to European Patent Application No. 09009804.7, filed on Jul. 29, 2009, the entireties of what are incorporated Herein by reference.

FIELD OF THE INVENTION

The present invention relates to a medical catheter, and more particularly, a balloon catheter having a reinforcing segment to facilitate catheter pushability and minimize kinking, balloon buckling and bunching.

BACKGROUND OF THE INVENTION

Angioplasty and stenting are widely used techniques for treating vascular disease. In balloon angioplasty, a catheter having an inflatable balloon affixed to its distal end is guided through a patient's vasculature with the balloon in a deflated state, and the balloon is positioned within a vascular lesion. The balloon then is inflated to compress the atherosclerotic plaque against the vessel wall to restore adequate blood flow in the vessel. Stenting involves the deployment of small tubular prostheses, either balloon expanded or self-expanding, that radially expand to maintain vessel patency, and are commonly used in conjunction with balloon angioplasty.

One problem associated with the use of balloon catheters is that kinks may develop along the catheter. Because the catheter must be relatively flexible to be advanced through tortuous vasculature, a flexible catheter is prone to kink when pushed from its proximal end by the physician. This is especially so when the distal catheter tip encounters resistance from a tight stenosis. The term "pushability" describes the ability of a catheter to transmit longitudinal forces from the proximal to the distal end, without creating kinks, and this is an integral characteristic of a successful catheter design.

Previously-known balloon catheters have attempted to enhance pushability primarily by reinforcing a proximal segment of the catheter. U.S. Pat. No. 5,626,600 to Horzewski et al. (Horzewski) describes a balloon dilatation catheter comprising proximal and distal extremities, an inflation lumen extending therethrough, a balloon disposed on the distal extremity that communicates with the inflation lumen, and a separate guidewire lumen. A small plug may be disposed within the guidewire lumen to separate the guidewire lumen into a proximal stiffening section and distal guidewire section. A stiffening mandrel may be inserted into the proximal stiffening section of the guidewire lumen, proximal to the plug, to influence proximal stiffness and to enhance pushability of the catheter. According to the patent, the apparatus strives to enhance catheter pushability by proving a catheter having a stiff proximal portion, a soft distal portion and a very soft low profile tip portion.

One drawback associated with the catheter described in the Horzewski patent is the potential for kinks to develop at the distal end of the catheter, i.e., near the balloon. The stiff proximal section may be readily advanced, but the location where the soft distal portion joins the stiff proximal section may be particularly susceptible to kinking. This adverse event is especially likely to occur when the very soft distal section is attempted to be pushed through a tight stenosis because there is no distal reinforcement.

Furthermore, the distal end of the above-described balloon catheter would be particularly susceptible to kink when used during a stenting procedure. This is because mounting a stent over the balloon increases the rigidity of the soft distal section, and the joint between the soft and rigid segments is susceptible to kink when the catheter is pushed forcefully.

Other catheter designs have provided an outer tube that extends through the balloon segment to the distalmost end of the catheter. U.S. Pat. No. 5,085,636 to Burns (Burns) describes a catheter comprising an elongated flexible tube having an inflatable balloon at its distal end. There is one single lumen for both the guidewire and inflation/deflation functions, as a pair of distal valves provide a fluid tight seal around the guidewire during inflation and deflation of the balloon. The patent suggests that the elongated flexible tube that extends to the distalmost end of the catheter may be of an integral or multipart construction.

The Burns patent specifically recommends manufacturing the proximal section from "hypotube" (stainless steel hypodermic needle tube), while the distal segment comprises a flexible polymer tube. Like the Horzewski device, Burns strives to increase overall pushability by providing a primarily reinforced proximal segment. However, like the device described in the Horzewski patent, the flexible distal end of the device in the Burns patent still will be susceptible to kinking, when it encounters a tight stenosis. In particular, kinking may occur at the proximal balloon connection because at this location a flexible polymer tube section is disposed between the stiff hypotube section and the relatively stiff balloon section.

In view of these drawbacks of previously known balloon catheters, it would be desirable to provide apparatus that increases the push force transmitted from the outer tube to the distal end of the catheter, e.g., to facilitate pushability of the distal end through a tight stenosis.

It still further would be desirable to provide apparatus having an increase in the relative compressive stiffness of the tubular inner and outer members of an angioplasty catheter while maintaining the high flexibility of the catheter especially in the distal portion of the catheter.

It still further would be desirable to provide apparatus that minimizes the formation of kinks near the distal end of a balloon catheter.

SUMMARY OF THE DISCLOSURE

In view of the foregoing, it is an object of the present invention to provide apparatus that increases the push force transmitted from the outer tube to the distal end of the catheter, e.g., to facilitate pushability of the distal end through a tight stenosis.

It is another object of the present invention to provide apparatus having an increase in the relative compressive stiffness of the tubular inner and outer members of an angioplasty catheter while maintaining the high flexibility of the catheter especially in the distal portion of the catheter.

It is another object of the present invention to provide apparatus that minimizes the formation of kinks near the distal end of a catheter.

These and other objects of the present invention are accomplished by providing apparatus suitable for enhancing distal pushability of a catheter. The apparatus preferably comprises a catheter having an outer tube, an inner guidewire tube that extends coaxially within the outer tube, and—preferably—a balloon disposed near the distal end of the catheter. The balloon is affixed at a proximal affixation point to the outer tube, and affixed at a distal affixation point to the inner tube. If the apparatus is in the form of a balloon catheter, the outer lumen defined between the coaxially disposed inner tube and outer tube is an inflation lumen. The apparatus further comprises a load-sharing member imposed on the inner tube at a distal portion proximal of the distal end of the outer tube which is configured to form a reversible mechanical linkage between inner tube and outer tube while an axially compressive load is applied to the catheter tip.

In one embodiment according to the present invention the load-sharing member has two fixation areas where the load-sharing member is fixed to the inner tube and a connecting body extending therebetween, and wherein the connecting body is configured to radially expand while an axially compressive load is applied to the catheter tip. This is usually happening while effectively foreshortening the load-sharing member. Usually and as a preferred aspect of this embodiment the said radial expansion establishes the reversible mechanical linkage. Therefore, in this embodiment according to the present invention the load-sharing member has two fixation areas where the load-sharing member is fixed to the inner tube and a connecting body extending therebetween, and wherein the connecting body is configured to radially expand while an axially compressive load is applied to the catheter tip thereby establishing the said reversible mechanical linkage.

In one embodiment according to the present invention the load-sharing member has a tubular form. From hereon this specific type of load-sharing member will also be called "tubular member". This tubular member has an annular wall with a number of cuts extending through it. The cuts through the annular wall of the tubular member may be of a helical pattern, of a lattice pattern or of a longitudinal parallel shaped pattern. Preferably, the tubular member further comprises fixing collars at its distal and its proximal end to facilitate fixation of the tubular member on the outer wall of the inner tube.

BRIEF DESCRIPTION OF THE DRAWINGS

Further features of the invention, its nature and various advantages will be more apparent from the accompanying drawings and the following detailed description of the preferred embodiments, in which.

DETAILED DESCRIPTION

Figure 1:
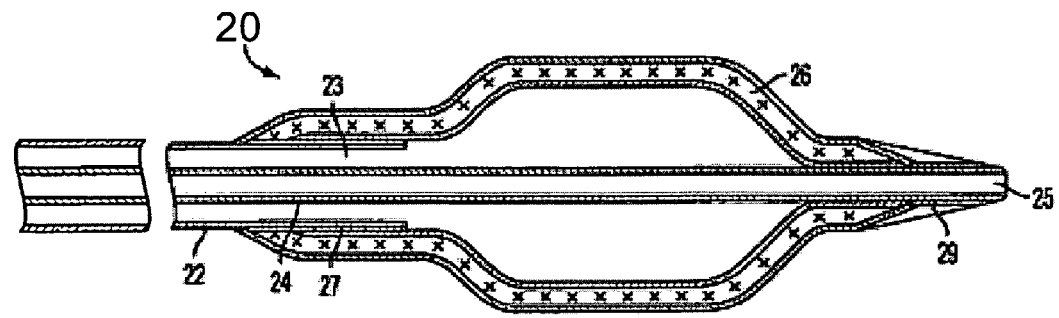
FIG. 1 is an illustration of the distal end of a previously-known coaxial catheter design.

Referring to FIG. 1, a previously-known balloon catheter from U.S. Pat. No. 5,492,532 to Ryan et al. (Ryan) is described. Catheter 20 comprises outer tube 22, inner tube 24, and balloon 26 having proximal and distal ends, the proximal end of balloon 26 being affixed to outer tube 22 at proximal affixation point 27 and distally affixed to inner tube 24 at point 29. Outer tube 22 and inner tube 24 are provided in a coaxial alignment, such that inflation lumen 23 communicates with balloon 26 while guidewire lumen 25 allows catheter 20 to be advanced over a guidewire. Catheter 20 comprises proximal and distal ends, of which the distal end is depicted in FIG. 1. The proximal end of catheter 20 communicates with a traditional proximal hub assembly (not shown) that comprises a proximal guidewire entry port and an inflation/deflation port. The apparatus further may comprise radiopaque markers (not shown) affixed to inner tube 24 and disposed within balloon segment 26.

One drawback associated with this previously-known design is that outer tube 22 and inner tube 24 are not connected to each other along the length of the catheter. Consequently, the axial load to the catheter tip has to be carried by the inner tube alone. Therefore, the inner tube 24 will be susceptible to kinking when the distal end of catheter 20 is advanced into a tight stenosis. The push force provided at the proximal end of catheter 20 may not be fully transmitted to the distalmost end of catheter 20, in part because outer tube 22 terminates at the proximal balloon sleeve 27.

Figure 2:
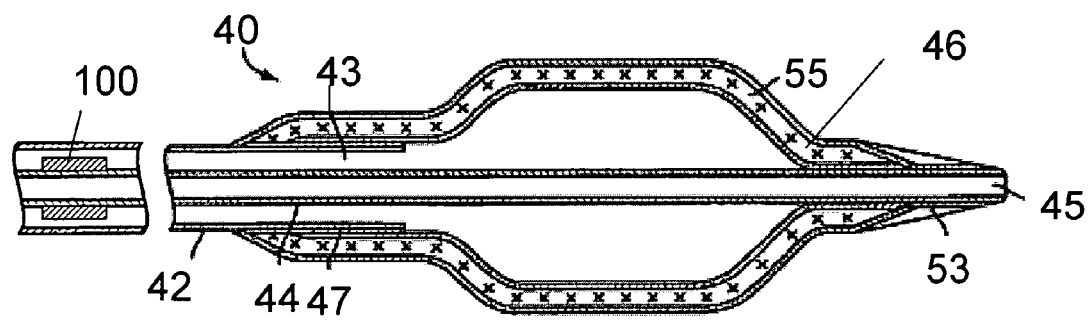
FIG. 2 is an illustration of the distal end of a catheter according to the present invention.

Referring now to FIG. 2, catheter 40 constructed in accordance with principles of the present invention is described. Catheter 40 comprises proximal and distal ends, of which the distal end is depicted in FIG. 2. The proximal end of catheter 40 communicates with a traditional proximal hub assembly (not shown) that comprises a proximal guidewire entry port and—preferably—an inflation/deflation port.

The distal end of catheter 40 comprises outer tube 42, inner tube 44 and balloon 55, each having proximal and distal ends. Inner tube 44 extends coaxially within outer tube 42 and extends beyond the distal end of balloon 46. The guidewire lumen 45 communicates with the guidewire entry port and if the inner lumen 43 is an Inflation/deflation lumen it communicates with a proximal inflation/deflation port. Guidewire lumen 45 of inner tube 44 is configured to permit the advancement of catheter 40 over guidewire 50.

The proximal end of balloon 55 is affixed to outer tube 42 at proximal affixation point 47, e.g., using a solder, weld or biocompatible adhesive, while the distal end of balloon 46 is affixed to inner tube 44 at distal affixation point 53, as shown in FIG. 2. The area extending between proximal and distal affixation points 47 and 53 defines balloon segment 55. The apparatus preferably further comprises radiopaque markers 48 (not shown) affixed to inner tube 44 and disposed within balloon segment 55.

In accordance with principles of the present invention, a load-sharing member 100 is imposed on the inner tube 44 at a preferably distal portion proximal of the distal end of the outer tube 42. The load-sharing member 100 is configured to form a reversible mechanical linkage between inner tube 44 and outer tube 42 while an axially compressive load is applied to the catheter tip. In the absence of an axially compressive load the load-sharing member 100 and the outer tube 42 are not linked to each other. The load-sharing member is in tubular form (a tubular member) having an annular wall with a number of recesses or cuts extending through it. Thus, the tubular member 100 does not block the annular space between the inner tube and the outer tube, the inner lumen, preferably required for balloon in/deflation, and preferably does decrease the profile of the in/deflation lumen only to a low or even negligible degree both, in the absence and in the presence of an axial load.

The characteristics of outer tube 42 and inner tube 44, respectively, may vary along its length to influence stiffness at selected locations, particularly to provide increased stiffness along balloon segment 55. The characteristics of outer tube 42 and inner tube 44, respectively, may be varied regionally by providing a rigid section, braided or spiral-shaped section. Outer tube 42 and inner tube 44, respectively, may be manufactured using a single-wall tubing, or may be provided as co-extruded tubing to allow for different surface properties inside and outside the tubing. The characteristics of catheter 40 further may be altered by manufacturing outer tube 42 and inner tube 44, respectively, using at least one material along its length, e.g., a combination of different polymeric materials using adhesives or advanced extrusion techniques. It should be appreciated that providing different materials and/or varying the textures of outer tube 42 and inner tube 44, respectively, at any combination of locations is intended to fall within the scope of the present invention.

Referring now to FIGS. 3 to 9 further details of the load-sharing member, different embodiments and their functionality are illustrated.

As already mentioned above, the purpose of the load-sharing member 100—also if being a tubular member having an annular wall with a number of cuts or recesses through it—is to increase the relative compressive stiffness of the tubular inner 44 and outer tubes 42 of an angioplasty catheter and provide a mechanical linkage between both tubes to assist with carrying the axial compressive load, thus reducing the load carried by either individual tube thus improving push efficiency transmission, and reducing balloon buckling and bunching.

For a conventional angioplasty catheter having uniform properties along its inner 44 and outer tubes 42 the axial load carried by the catheter, especially the balloon catheter, depends essentially on three factors; (1) the axial compressive load carried by the balloon to the catheter tip, (2) the relative compressive stiffness value for the inner member and balloon, and (3) the length of the balloon relative to the inner member. The ability to transmit force to the distal tip of the catheter is essential in optimizing push characteristics.

The apparatus according to the present invention overcomes some of the inherent disadvantages of prior art by providing a mechanical connection between both the inner and outer tubes only when necessary, increasing the relative stiffness, proportionally, as axial load is applied to the distal tip of the angioplasty catheter. Prior art has focused ostensibly on the use of similar materials and spiral cut designs, which are affixed to the inner tube only, and work by stiffening the inner tube component only. They do not form this mechanical bond to "load-share" with the outer tubular tube. Prior art has also relied on the use of multiple polymer segments decreasing in durometer proximally to distally. The apparatus of the present invention also addresses this, enabling the use of softer materials.

The component consists of a load-sharing member 100 preferably having two fixation areas where the load-sharing member is preferably fixed to the inner tube and a connecting body extending therebetween, wherein the connecting body is configured to radially expand while an axially compressive load is applied to the catheter tip.

In a preferred embodiment the load-sharing member 100 is a tubular member having an annular wall with a number of preferably symmetrical cuts or recesses through it. In the various embodiments the cuts form patterns including helical, lattice, or longitudinal parallel shaped patterns. The suitable patterns of the tubular member 100 can be achieved by either removing material from a solid tubular member or by arranging wires, bands or threads in the desired configuration to form the tubular member.

In a preferred embodiment, the cuts are uniformly and symmetrically distributed both circumferentially and longitudinally about the outer diameter and length of the tubular member. The tubular member 100 does not necessarily contain but may contain variable pitch cuts, and therefore does not have a specific distal or proximal orientation. Its purpose is not designed to act as a transitional member aiding transition from higher durometer materials to lower durometer materials, but instead is designed to be placed advantageously within the lumen of the outer tube 42 with its outer circumference juxtaposed to the inner circumference of the outer tube 42. The fit between them should be an interference or frictional fit. The tubular member 100 is affixed at one or both ends to the inner tube 44 by for example but not limitation mechanically by crimping the fixing collars about the circumference of the inner member, or by using an adhesive bond or both. In a further embodiment, the tubular member 100 may also be attached to the outer tube 42 of the angioplasty catheter.

As an axial compressive load is applied to the tip of the catheter the inner and outer members 44 and 42, and balloon 46 are inclined to compress due to their elastic behavior. Catheters according to the present invention comprising the load-sharing member within the lumen of the outer tube 44, the compressive forces compel the load-sharing member to expand radially as its length is effectively shortened. This forms a mechanical linkage between inner and outer tubes, thus sharing the applied load and preventing the loss of push efficiency to the tip.

In an alternative embodiment the catheter may include not only one but 2, 3, 4 or even more of the load-sharing members placed along the length of the inner tube.

In a further embodiment a load-sharing member may be placed in the balloon region, thus reducing the risk of balloon buckling and bunching.

Figure 3:
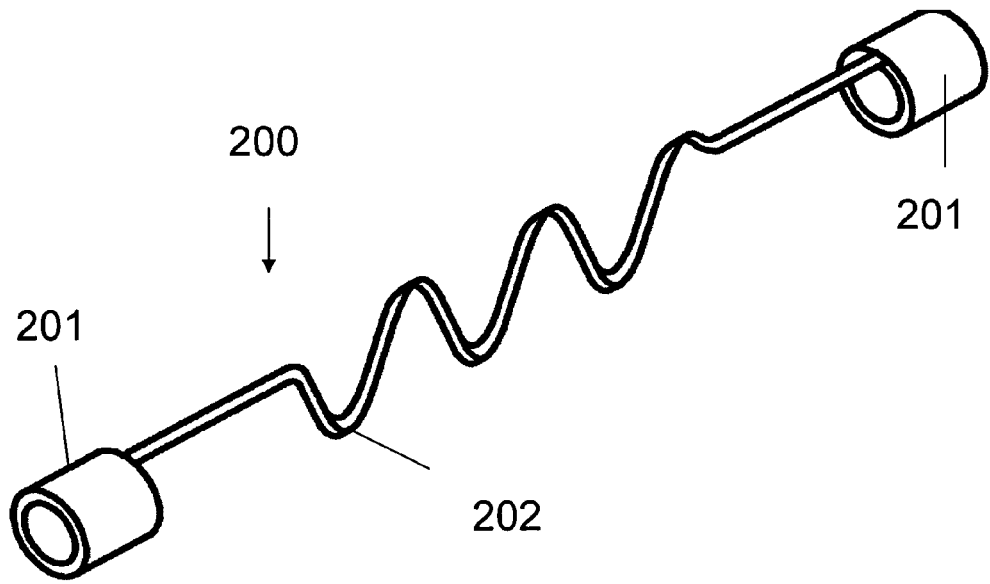
FIG. 3 is a schematic illustration of one embodiment of the load-sharing member according to the invention.

FIG. 3 is an illustration of a preferred embodiment of the load-sharing/tubular member 200 according to the present invention. The tubular member 200 is cut in a helical configuration including a fixing collar 201 on each end of the member. A spiral or helical members 202 stretch between the fixing collars. In this embodiment the inner tube feeds coaxially through the fixing collars 201 and between the helical members 202.

Figure 4:
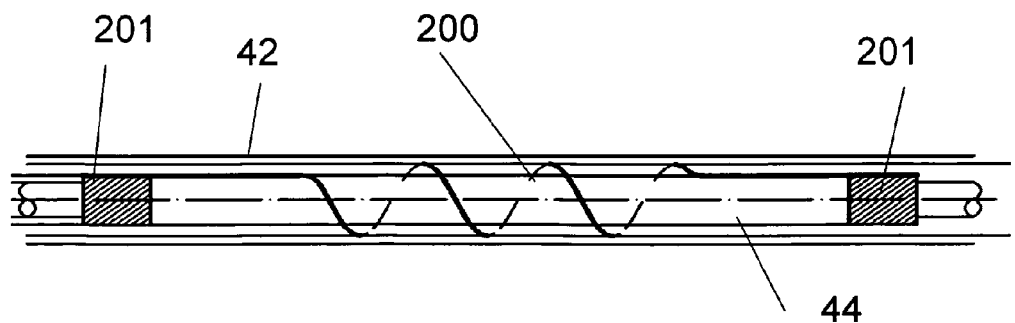
FIGS. 4, 5 and 6 depict a cross sectional view of the catheter shaft of a catheter according to the present invention including the load-sharing member imposed on the inner tube.

FIG. 4 illustrates the embodiment of the tubular member already depicted in FIG. 3 mounted on the inner tube 44 of a catheter according to the present invention. The outer tube 42 is disposed coaxially over the inner tube 44 and the tubular member 200 leaving an (inner lumen) annular in/deflation space between inner and outer tube. The tubular member 200 is cut in the helical configuration and positioned juxtaposed within the inner circumference of the outer tube 42, and fixed either distally or proximally or both with the fixing collars 202 to the inner tube 44.

Figure 5:
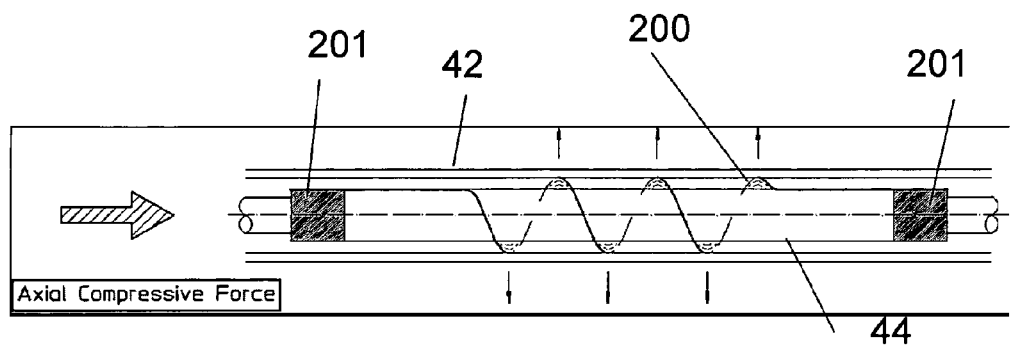

FIG. 5 illustrates the motion of the helical tubular member 200 when a compressive axial force is applied to the tip of the catheter. The helical load-sharing/tubular member 200 expands pressing itself against the inner circumference of the outer tube thereby forming a mechanical linkage and providing load-sharing support, and thus improving push efficiency.

Figure 6:
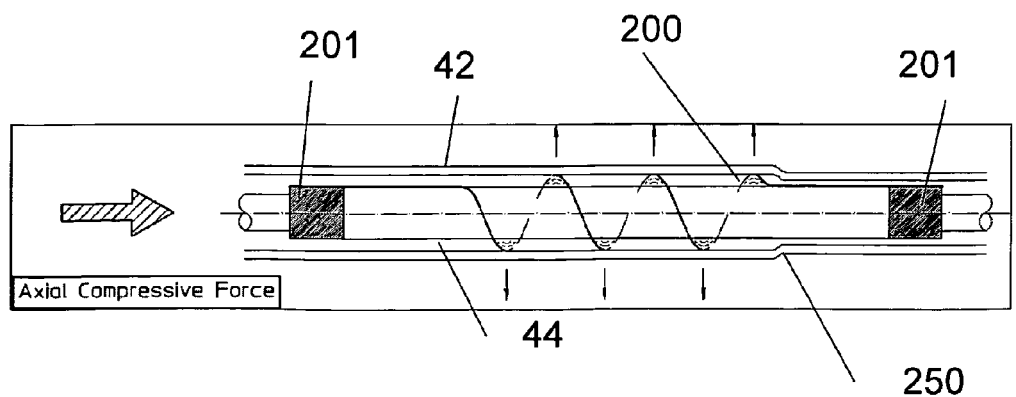

FIG. 6 shows an alternative fixation of the load-sharing/tubular member 200 into the outer tube, whereby the outer tube is drawn down, i.e. has a taper down 250 in diameter just distal to the tubular member. In this embodiment the tubular member is augmented in deploying outwards, and forming the mechanical linkage to the outer tube 42.

Figure 7:
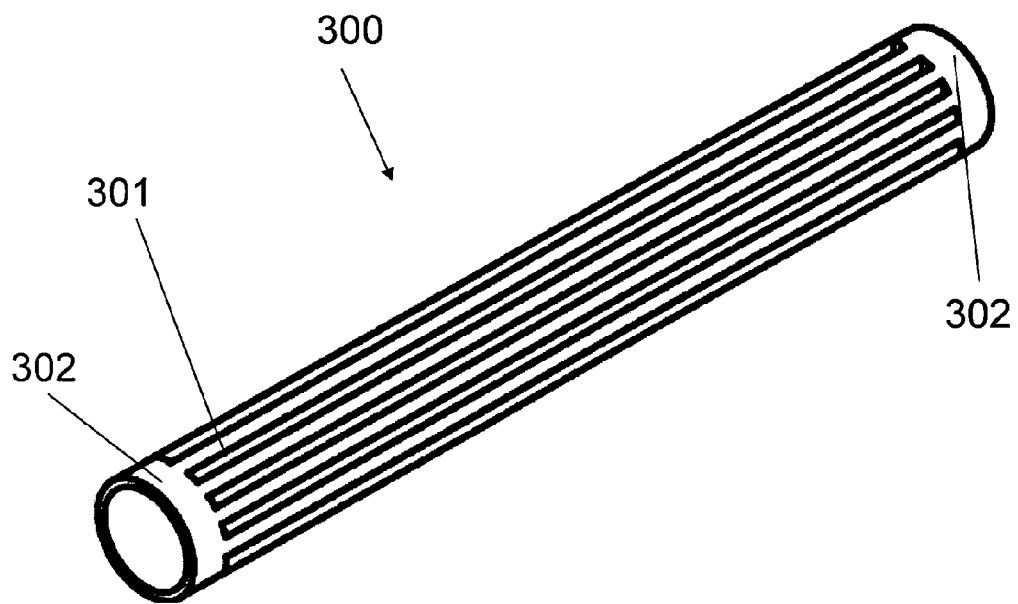
FIGS. 7 and 8 describe an alternative embodiment of the load-sharing member of the present invention.

FIG. 7 illustrates another embodiment of the present invention. The load-sharing/tubular member 300 has a parallel slotted configuration, i.e. slots 301 parallel to the longitudinal axis of the tubular member 300 are cut into the annular wall, keeping the proximal and distal fixing collars 302. This alternative embodiment of the tubular/load-sharing member 300 is positioned onto the inner tube of the catheter in exactly the same way as the helically cut embodiment.

Figure 8:
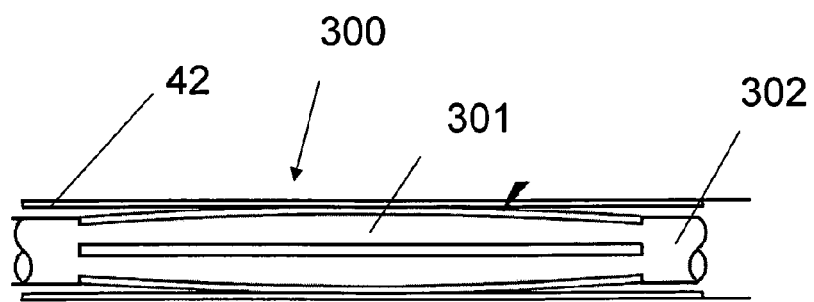

FIG. 8 shows how the load-sharing/tubular member according to the embodiment depicted in FIG. 7 of the present invention deploys itself when an axial longitudinal force is applied to the tip of the angioplasty catheter forming a mechanical bond to the outer tube 42 (inner tube is not shown).

Figure 9:
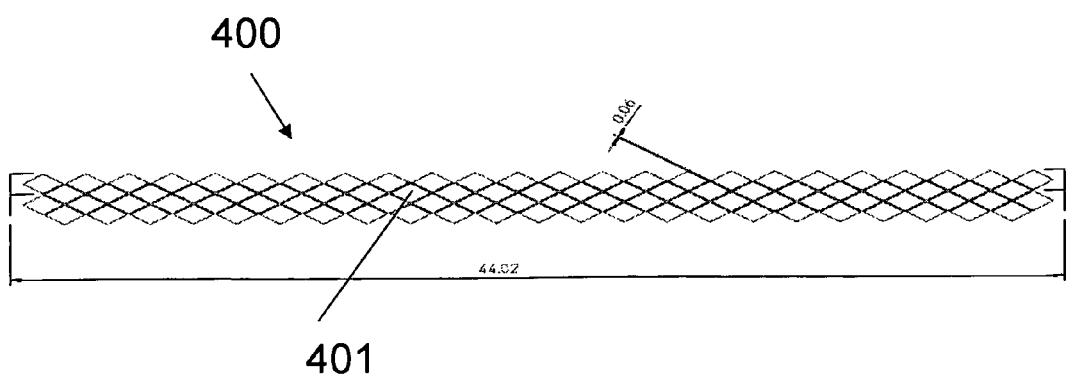
FIG. 9 describes a further alternative embodiment of the load-sharing member of the present invention.

FIG. 9 illustrates yet another alternative embodiment of the load-sharing/tubular member 400 according to the present invention. The tubular member 400 is cut in the form of a lattice structure 401. In a preferred embodiment, also fixing collars are kept at the both ends of the tubular/load-sharing member 400 (not shown). This alternative embodiment of the load-sharing/tubular member 400 is positioned onto the inner tube of the catheter in exactly the same way as previous embodiments with the use of collars, and functions mechanically in an identical fashion to the previous components.

In further embodiments according to the present invention the load-sharing/tubular member 400 may be cut in the form of any pattern known as stent designs that exhibits a certain degree of foreshortening, i.e. any pattern that allows the tubular/load-sharing member to increase in diameter or radially expand upon application of axial load or axial shortening.

The load-sharing/tubular member may be produced from elastic materials like for example but not limitation a stainless steel hypotube, or other metallic elements, especially in tubular form, like for example amalgams such as Nitinol, or alternatively stiffer polymers e.g., composite or reinforced polymers, or other suitable materials.

While preferred illustrative embodiments of the invention are described above, it will be apparent to one skilled in the art that various changes and modifications may be made therein without departing from the invention. The appended claims are intended to cover all such changes and modifications that fall within the true spirit and scope of the invention.

What is claimed is:

1. Apparatus suitable for enhancing pushability of a balloon catheter, the apparatus comprising:
   an outer tube having proximal and distal ends; an inner tube having proximal and distal ends and a guidewire lumen extending therethrough, the inner tube disposed coaxially within the outer tube to define an inner inflation lumen therebetween;
   wherein a load-sharing member is imposed on the inner tube at a portion proximal of the distal end of the outer tube, and wherein the load-sharing member is configured to form a reversible mechanical linkage between inner tube and outer tube, while maintaining inner inflation lumen patency, while an axially compressive load is applied to a catheter tip;
   wherein the apparatus further comprises a balloon having proximal and distal ends, wherein the proximal end of the balloon is affixed to the outer tube at a proximal affixation point and the distal end of the balloon is affixed to the inner tube at a distal affixation point to define a balloon segment extending therebetween;
   wherein the load-sharing member has two fixation areas where the load-sharing member is fixed to the inner tube and a connecting body extending therebetween, and wherein the connecting body is configured to radially expand while an axially compressive load is applied to the catheter tip, thereby establishing the said reversible mechanical linkage; and
   wherein the load-sharing member has a tubular form being a tubular member having an annular wall with a number of recesses extending through it; the number of recesses extending through the tubular member to maintain inner inflation lumen patency while the axially compressive load is applied to the catheter tip.

2. The apparatus of claim 1 wherein shapes of the recesses through the annular wall of the tubular member are selected from a group consisting of a helical pattern, a lattice pattern, and a longitudinal parallel shaped pattern.

* * * * *